United States Patent
Shapiro et al.

(10) Patent No.: US 6,628,111 B2
(45) Date of Patent: Sep. 30, 2003

(54) METHOD AND APPARATUS FOR CORROSION SENSING

(75) Inventors: Andrew Philip Shapiro, Schenectady, NY (US); Roger Warren Haskell, Scotia, NY (US)

(73) Assignee: General Electric Company, Niskayuna, NY (US)

( * ) Notice: Subject to any disclaimer, the term of this patent is extended or adjusted under 35 U.S.C. 154(b) by 0 days.

(21) Appl. No.: 09/681,529

(22) Filed: Apr. 24, 2001

(65) Prior Publication Data

US 2002/0153873 A1 Oct. 24, 2002

(51) Int. Cl.[7] .................. G01N 27/00; G01R 27/08
(52) U.S. Cl. .............. 324/71.2; 324/700; 324/71.1
(58) Field of Search .................. 324/71.2, 71.1, 324/700, 701, 715; 73/86

(56) References Cited

U.S. PATENT DOCUMENTS

| | | | |
|---|---|---|---|
| 3,617,685 A | * 11/1971 | Brill-Edwards | 219/121.4 |
| 4,380,763 A | * 4/1983 | Peart et al. | 324/700 X |
| 4,684,884 A | * 8/1987 | Soderlund | 324/71.1 |
| 4,755,744 A | * 7/1988 | Moore et al. | 324/71.2 |
| 4,780,664 A | * 10/1988 | Ansuini et al. | 324/700 |
| 4,896,965 A | 1/1990 | Goff et al. | 356/417 |
| 5,150,065 A | * 9/1992 | Luna | 324/700 |
| 5,166,626 A | * 11/1992 | Hester et al. | 324/690 |
| 5,171,517 A | * 12/1992 | Solomon et al. | 376/245 |
| 5,286,357 A | * 2/1994 | Smart et al. | 204/153.11 |
| 5,406,193 A | 4/1995 | Sethi | 324/71.1 |
| 5,627,749 A | * 5/1997 | Waterman et al. | 364/422 |
| 5,792,337 A | * 8/1998 | Padovani et al. | 205/775.5 |
| 5,854,557 A | * 12/1998 | Tiefnig | 324/700 |
| 5,895,843 A | * 4/1999 | Taylor et al. | 324/700 X |
| 5,977,782 A | * 11/1999 | Kordecki | 324/700 |
| 6,153,313 A | * 11/2000 | Rigney et al. | 428/632 |

* cited by examiner

Primary Examiner—N. Le
Assistant Examiner—T. R. Sundaram
(74) Attorney, Agent, or Firm—Penny A. Clarke; Patrick K. Patnode

(57) ABSTRACT

A corrosion sensor for use within a fluid flow path includes a sensing element and circuitry coupled to the sensing element for detecting corrosion of the sensing element. Another embodiment of a corrosion sensor for use within a fluid flow path comprises a hermetic housing, a sensing element attached to an external portion of the housing for exposure to the fluid flow path, and circuitry disposed within said hermetic housing, which circuitry is coupled to the sensing element for detecting corrosion of the sensing element.

36 Claims, 4 Drawing Sheets

METHOD AND APPARATUS FOR CORROSION SENSING

BACKGROUND OF INVENTION

This invention relates to the detection of corrosion of structural materials within a fluid flow path. More particularly, the invention relates to a method and apparatus for detecting corrosive contaminants in combustion gases in gas turbines. Even more particularly, the invention relates to a method and apparatus for detecting corrosive alkali metal contaminants in combustion gases in gas turbines.

Many structures, such as aircraft and power turbine assemblies, reactors and cracking columns in chemical plants and refineries, blast furnaces, and nuclear reactors, include structural components that are exposed to fluid flows containing potentially corrosive contaminants. For example, advanced gas turbines, designed for power generation, use metal alloys that are selected to provide maximum strength at the high temperatures encountered in the first stage buckets. As a result, such alloys are less resistant to hot corrosion than alloys operating at lower temperatures.

The presence of sodium and other alkali metals in fuel, air, water, or steam supplied to the combustion chambers of gas turbines can create a gaseous mixture that is corrosive to the high temperature alloys used in a hot gas path. Alkali metals may initially be present as salts in either the fuel or air ingested by a turbine assembly. Seawater, for example, may mix with fuel transported in tanker ships. Similarly, turbine assemblies sited on or near a coastline ingest air having a high salt content. Alkali metal salts, once ingested, may combine with sulfur in the fuel to form alkali metal sulfates that condense or impinge upon turbine components. Metals present within the alloys, such as nickel, cobalt or iron, may react with the molten alkali sulfates to form a corrosive liquid over a wide temperature range, resulting in the phenomena known as hot corrosion. Hot corrosion leads to a considerable reduction in the life of turbine components.

Techniques are presently available for detecting and measuring the concentrations of corrosion-causing species in turbine supply lines. The concentration of sodium in fuel oil, for example, can be measured by atomic absorption, inductively coupled plasma (ICP)/atomic emission, and mass spectroscopy. These analytical methods are designed for use under laboratory conditions and are not commonplace in industrial settings, such as those encountered at power generation facilities. In addition to the above-mentioned techniques, sodium ion selective electrodes can also be used to measure sodium concentrations in aqueous media, and ion chromatography has also been employed for alkali metal detection. None of these technologies has been applied to monitor the combustion gases in a gas turbine, and none provide a direct indication of the corrosivity of the gases.

Although sensors are currently being used to monitor sodium levels in water and other systems are being developed to measure sodium in fuels, it is impractical to measure the presence of sodium or other potentially corrosive contaminants in a fluid flow path, such as the air that is supplied to a gas turbine. Therefore, what is needed is a sensor capable of detecting the total amount of corrosive contaminants, such as sodium or other alkali metals, in a fluid flow path. What is also needed is a sensor capable of measuring the degree of corrosion of structural components exposed to such a fluid flow path.

SUMMARY OF INVENTION

A corrosion sensor for use within a fluid flow path includes a sensing element and circuitry coupled to the sensing element for detecting corrosion of the sensing element. Another embodiment of a corrosion sensor for use within a fluid flow path comprises a hermetic housing, a sensing element attached to an external portion of the housing for exposure to the fluid flow path, and circuitry disposed within said hermetic housing, which circuitry is coupled to the sensing element for detecting corrosion of the sensing element.

These and other aspects, advantages, and salient features of the invention will become apparent from the following detailed description, the accompanying drawings, and the appended claims.

DETAILED DESCRIPTION

Figure 1:
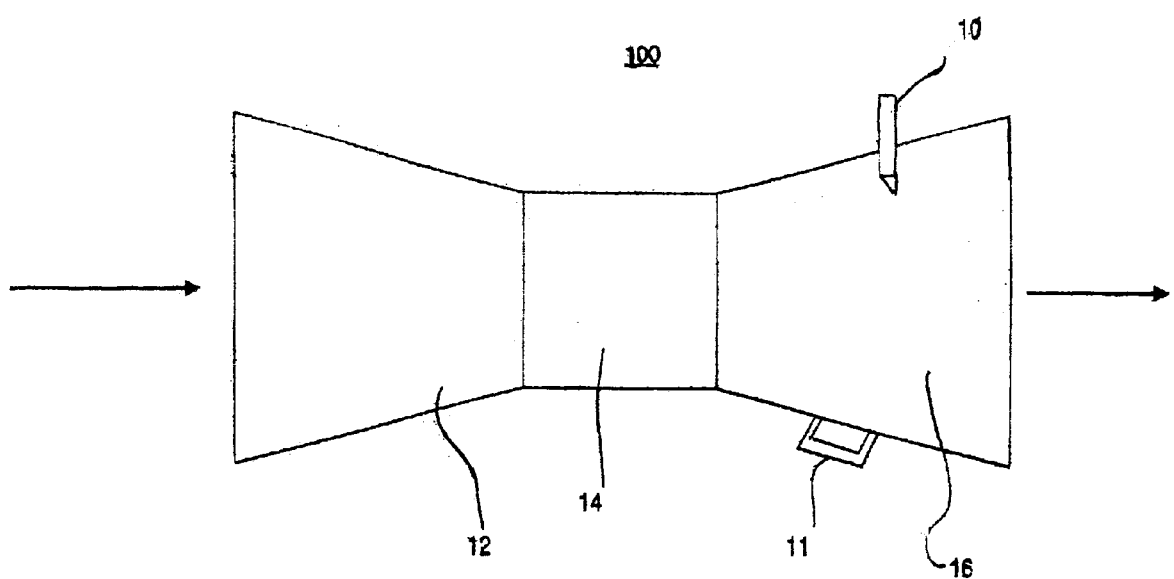
FIG. 1 is a schematic representation of a turbine assembly having a corrosion sensor of the present invention.

In the following detailed description, like reference characters designate like or corresponding parts throughout the several views shown in the figures. It is also understood that terms such as "top," "bottom," "outward," "inward," and the like are words of convenience and are not to be construed as limiting terms.

Referring to the drawings in general and to FIG. 1 in particular, it will be understood that the illustrations are for the purpose of describing a preferred embodiment of the invention and are not intended to limit the invention thereto. FIG. 1 is a schematic diagram of a turbine assembly 100 of the present invention. The turbine assembly 100 may either be a land-based turbine, such as those widely used in power generation, or an aircraft engine. Air enters the turbine assembly 100 and is first compressed in the compressor section 12 of the turbine assembly 100. The high-pressure air then enters the combustor 14 where it is combined with a fuel, such as natural gas, diesel fuel, or jet fuel, and is burned. The hot, high-pressure air exiting the combustor 14 is then expanded through a series of turbine stages and then through an exhaust section 16 of the turbine assembly 100, where energy is extracted to generate power. Components found within the combustor 14 and exhaust section 16, such as wheels, rotors, vanes, buckets, nozzles, and the like, are most susceptible to corrosion caused by contaminants found in either the fuel or air ingested by the turbine assembly 100.

The turbine assembly 100 comprises components that are formed from alloys, such as Rene N5 and other superalloys, having low chromium content. While such alloys have the required strength for turbine applications, they are susceptible to corrosion by gaseous species that contain alkali metals, such as sodium or potassium. Alkali metals may initially be present as salts in either the fuel or air that is ingested by the turbine assembly 100. Seawater, for example, may mix with fuel transported in tanker ships. Similarly, turbine assemblies sited on or near a coastline ingest air having a high salt content. Alkali metal salts, once ingested, combine with sulfur in the fuel to form the corresponding alkali metal sulfates, such as $Na_2SO_4$ and $K_2SO_4$. At the temperatures encountered within the combustor 14 (about 1600° F.), the alkali metal sulfates are molten. The molten alkali metal sulfates condense or impinge upon turbine components formed from metallic alloys. Nickel, cobalt or iron present within the alloys reacts with the molten alkali sulfates to form a corrosive liquid over a wide temperature range. For example, cobalt present within the alloys reacts with the molten sulfates to form a liquid eutectic mixture, such as $CoSO_4/Na_2SO_4$, thus corroding the turbine component.

The corrosion sensor 10 of the present invention provides in situ, real time measurement of the degree of corrosion of such alloys within the turbine assembly 100. Whereas other means of detecting contaminants detect contamination from a single upstream source, such as fuel or air, the corrosion sensor 10 offers the advantage of measuring the collective effect of the contaminants under conditions that closely approximate those under which corrosion is most likely to occur. A corrosion sensor 10 may, for example, be placed in the exhaust section 16 of the turbine assembly 100, such that the corrosion sensor 10 protrudes into the turbine exhaust stream. In this configuration, the corrosive species exiting the combustor 14 will directly condense or impinge on the corrosion sensor 10. Alternatively, the corrosion sensor 10 may be located in a slipstream 11, which diverts a portion of the turbine exhaust from the exhaust section 16 and directs the diverted exhaust onto the corrosion sensor 10. In a third embodiment, the corrosion sensor is placed in the hot gas path within the combustor section 14 of the turbine assembly 100.

In one embodiment of the invention, the corrosion sensor 10 of the present invention detects the degree of corrosion by imposing an oscillating electric field across a sensing element and directly measuring the degree of impedance of the oscillating electric field. The sensing element is at least as susceptible to corrosion as the materials present in the fluid flow path that are to be monitored. As the sensing element corrodes, the impedance changes. The change in impedance can be calibrated against a standard to provide a quantitative indicator of the degree of corrosion of selected materials within the fluid flow path.

Figure 2:
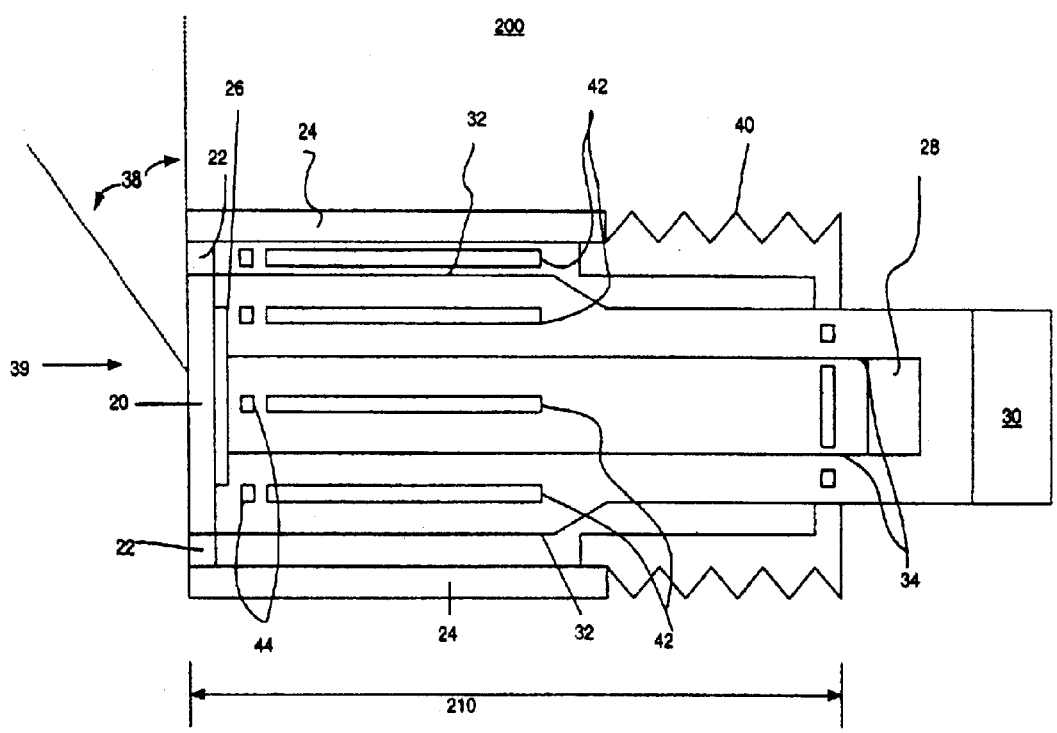
FIG. 2 is a schematic representation of another embodiment of the corrosion sensor of the present invention.

FIG. 2 shows one embodiment of the corrosion sensor 10 of the present invention. The corrosion sensor 200 comprises a probe 210 that is insertable into a fluid flow, such as an exhaust stream within the exhaust section 16 of the turbine assembly 100. The probe 210 includes a sensing element 20 formed from a metallic alloy and located at one end of the probe 210. In order to accurately gauge the corrosion of alloy components within the turbine assembly 100, the sensing element 20 is preferably a substantially planar coupon, having a thickness of between about 10 mils and about 50 mils, and is formed from a metallic alloy, such as a superalloy, that is used in components in either the combustor 14 or exhaust section 16. Alternatively, the sensing element 20 is formed from a nickel-base superalloy or the sensing element 20 is formed form either the alloy Udimet 700, an alloy quite sensitive to hot corrosion or the alloy Rene N5.

Typically, the surface of the planar sensing element 20 is oriented normal (90°) to the impinging fluid flow 39. However, the planar surface may be oriented such that the angle 38 between the surface and the fluid flow 39 is between 0° and 90°.

The probe 210 has an outer housing 24 formed from an alloy that is resistant to chemical attack at temperatures normally encountered in the fluid flow path. The sensing element 20 is separated from the outer housing 24 by a ceramic insulator 22. The ceramic insulator 22 prevents the sensing element from making electrical contact with the outer housing 24 and prevents material in the fluid flow path from entering the interior space of the outer housing 24.

The sensing element 20 is connected by a connector 32 to a processor 30 that is capable of detecting a signal therefrom and potentially to provide power to the sensing element 20. The signal generated by the sensing element 20 may be either an impedance signal or resistance signal. The signal may be either a time dependent signal or an on/off signal. The processor 30 may further include an alarm, shutdown switch, or the like, which is triggered when the signal generated by the sensing element 20 falls below a predetermined level.

As shown in FIG. 2, connector 32 typically comprises cables that are fed through the inner space and extend the length of the outer housing 24, exiting the outer housing 24 to connect the sensing element 20 to the processor 30. It is also contemplated, however, that a wireless means, such as a transmitter and receiver, may also be used to couple the sensing element 20 to the processor 30, thus permitting corrosion to be remotely monitored.

In the embodiment of the invention shown in FIG. 2, the corrosion sensor 200 is designed to be placed in the exhaust section 16 of a turbine assembly 100, where the temperature of the exhaust stream is typically between about 900° F. to about 1250° F. In order for the corrosion sensor 200 to accurately determine the degree of corrosion occurring at the higher temperatures within the combustor 14, the sensing element 20 itself needs to be heated to these higher temperatures. If the corrosion sensor 200 is not placed directly into a location exposed to these higher temperatures, the corrosion sensor 200 is additionally heated to the higher temperature by a heating module 26. The heating module 26 is preferably located within the outer housing 24 and contacts a surface of the sensing element 20 opposite the surface of the sensing element 20 exposed to the fluid flow 39. Preferably, the heating module 26 includes a resistance heater and a thermocouple for measuring the temperature of the heater and sensing element 20. Feedback from the thermocouple is provided by heater module connector 34 to a temperature controller and power supply 28 to regulate the temperature of the sensing element. Insulation, including, but not limited to, heat shields, tubing, and fibers formed refractory materials such as ceramics or refractory metals, may be placed in the free space within the interior of the outer housing 24 to increase the efficiency of the heater module 26 and prevent excessive damage to the probe 210.

In operation, the probe 210 is fitted into a wall of the exhaust section 16 of the turbine assembly 100 such that the sensing element 20 protrudes into the exhaust stream 39. A fitting 40, preferably a threaded fitting, located on the end of the probe 210 opposite the sensing element 20, is used to secure the probe 210 to the wall of the exhaust section 16.

Figure 3:
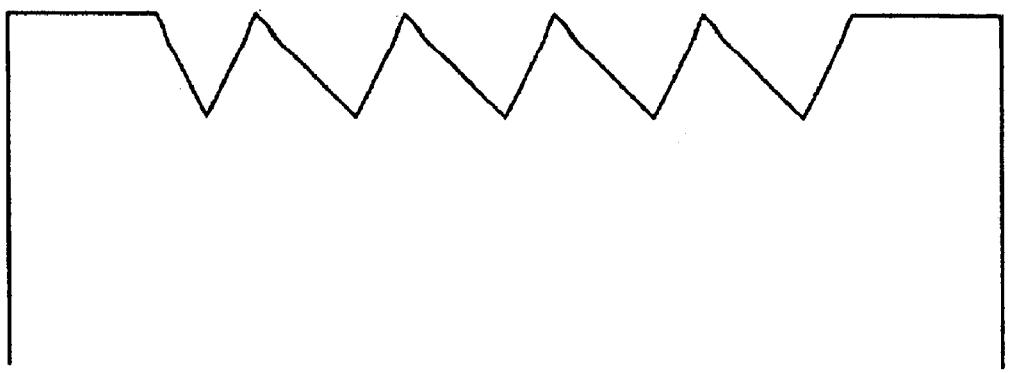
FIG. 3 is a schematic representation of a wire sensing element of the present invention.

In another embodiment of the invention, shown in FIG. 3, the sensing element 50 is formed from an alloy wire, typically having a diameter of between about 1 mil and about 5 mils. In this embodiment, the sensing element 50 acts as a fuse, corroding until electrical continuity is completely interrupted. In order to heat the sensing element 50 to the temperature range at which corrosion occurs, an electrical current is passed through the sensing element 50. Rather than detecting the variation of impedance over time, the processor 30 detects the sudden change in resistivity of the sensing element 50 due to corrosive failure.

Figure 4:
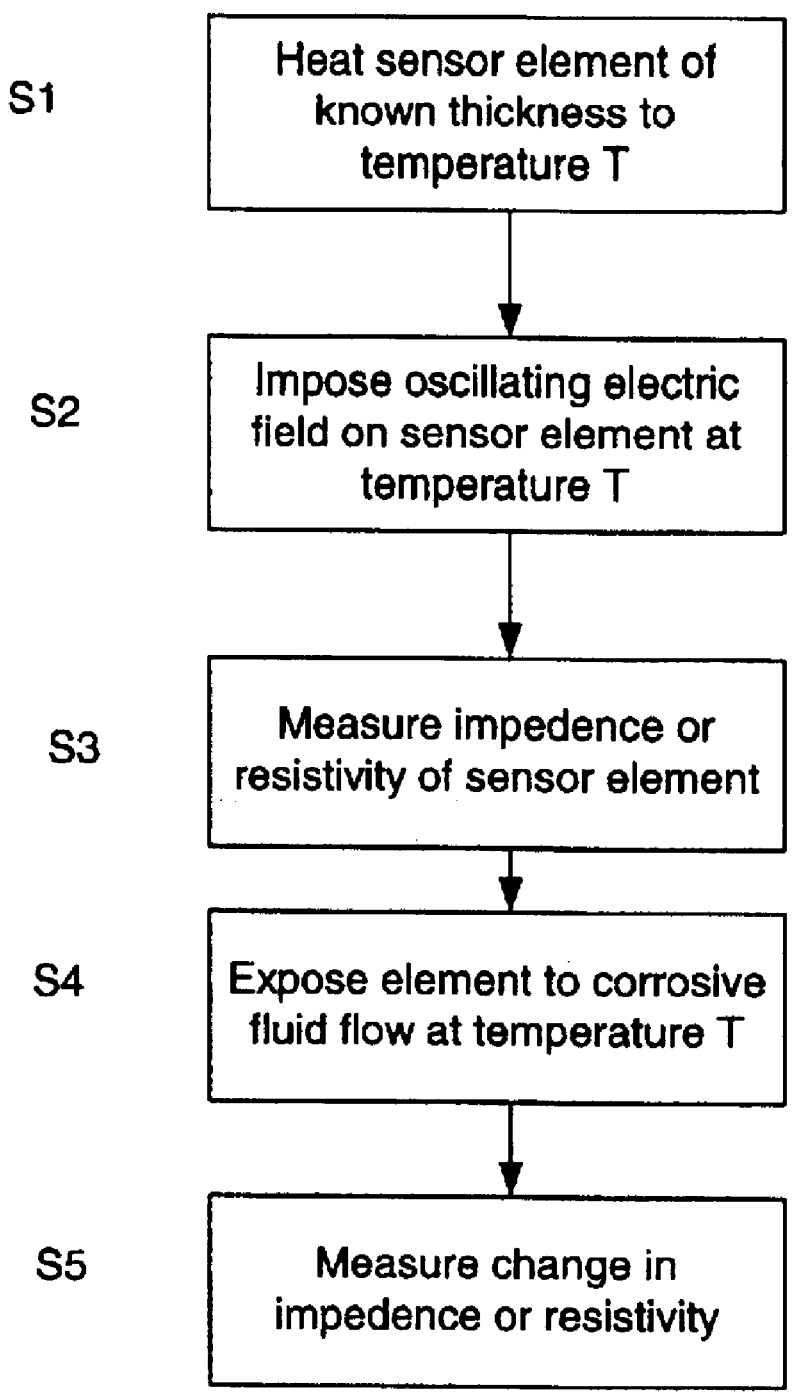
FIG. 4 is a flow chart showing a method of using the corrosion sensor of the present invention to detect corrosion in a fluid flow.

A method of using the corrosion sensor 10 of the present invention is outlined in FIG. 4. In step S1, the sensing element 20 is heated to the temperature T at which corrosion is to be measured. An oscillating electric field is then imposed on the sensing element 20 (step S2) and the impedance signal generated by the sensing element 20 is measured (step 53) to obtain a baseline value for the sensing element 20 in the absence of any substantial corrosion. The sensing element 20, which is maintained at temperature T in the presence of the oscillating electric field, is then exposed to the fluid flow in step S4. Contaminants within the fluid flow react with the sensing element 20, resulting in corrosion of the sensing element 20, which in turn causes a change in the impedance signal generated by the sensing element 20. The change in impedance of the sensing element 20 is measured (step S5), thereby providing an indicator of the degree of corrosion of the sensing element 20, which is indicative of the degree of corrosion experienced by other components within the fluid flow path. The degree of corrosion can be further quantified be separately performed tests in which the degree of corrosion is closely correlated with the impedance signal generated by a particular sensing element 20.

While only certain features of the invention have been illustrated and described herein, many modifications and changes will occur to those skilled in the art. For example, sensing elements having a geometry such as, but not limited to, tubular sections may be used. Also, the corrosion sensor 10 of the present invention may be used in structures other than a turbine assembly, in which structural materials are subjected to corrosion caused by the presence of contaminants in a fluid flow path. These structures include, but are not limited to, reactors and cracking columns in chemical plants and refineries, blast furnaces, and nuclear reactors. It is, therefore, to be understood that the appended claims are intended to cover all such modifications and changes as fall within the true spirit of the invention.

What is claimed is:

1. A corrosion sensor for use within a fluid flow path comprising:
    a sensing element being insertable within a fluid flow in at least one of a turbine assembly exhaust and a turbine assembly hot gas path;
    a heating module adapted to heat said sensing element; and
    circuitry coupled to said sensing element for detecting corrosion of said sensing element.

2. A corrosion sensor in accordance with claim 1, wherein said sensing element comprises an alloy.

3. A corrosion sensor in accordance with claim 2, wherein said alloy is a superalloy.

4. A corrosion sensor in accordance with claim 3, wherein said superalloy is a selected from the group consisting of a Ni-based superalloy, a Udimet 700 based superalloy, and a Rene N5 superalloy.

5. A corrosion sensor in accordance with claim 2, wherein said sensing element comprises a wire.

6. A corrosion sensor in accordance with claim 5, wherein said wire has a thickness in the range between about 1 mil to about 5 mil.

7. A corrosion sensor in accordance with claim 2, wherein said sensing element comprises a substantially planar coupon.

8. A corrosion sensor in accordance with claim 7, wherein said planar coupon has a thickness in the range between about 10 mil to about 50 mil.

9. A corrosion sensor in accordance with claim 1, wherein said circuitry comprises a processor for generating and detecting a current through said sensing element to detect corrosion of said sensing element.

10. A corrosion sensor in accordance with claim 9, wherein said sensing element is a wire and said corrosion is detected when said current is not detected through said sensing element.

11. A corrosion sensor in accordance with claim 9, wherein said sensing element is a planar coupon and said corrosion is detected by the level of impedance of said current through said sensing element.

12. A corrosion sensor in accordance with claim 11, wherein said level of impedance is used to detect the rate of corrosion of said sensing element.

13. A corrosion sensor in accordance with claim 1, wherein said heating module is configured to contact a first surface of said sensing element opposite to a second surface of said sensing element exposed to the fluid flow.

14. A corrosion sensor for use within a fluid flow path comprising:
    a hermetic housing;
    a sensing element attached to an external portion of said housing for exposure to said fluid flow path; and
    circuitry disposed within said hermetic housing, said circuitry being coupled to said sensing element for detecting corrosion of said sensing element, and said circuitry comprising a heating module configured to heat said sensing element to a predetermined temperature.

15. A corrosion sensor in accordance with claim 14, wherein said circuitry further comprises a processor for generating and detecting a signal through said sensing element.

16. A corrosion sensor in accordance with claim 15, wherein said signal is an impedance signal generated through said sensing element and is measured to detect corrosion of said sensing element.

17. A corrosion sensor in accordance with claim 16, further comprising at least one of an alarm or a shutdown switch coupled to said processor, which alarm or shutdown switch is activated when a measured impedance signal falls below a predetermined level.

18. A corrosion sensor in accordance with claim 14, wherein said sensing element is selected from the group consisting of an alloy, a superalloy, a nickel-based superalloy, a Udimet 700 alloy, and a Rene N5 alloy.

19. A corrosion sensor in accordance with claim 14, wherein said sensing element comprises a substantially planar coupon.

20. A corrosion sensor in accordance with claim 19, wherein said planar coupon has a thickness in the range between about 10 mil to about 50 mil.

21. A corrosion sensor in accordance with claim 19, wherein said planar coupon is disposed substantially normal to said fluid flow path.

22. A corrosion sensor in accordance with claim 19, wherein said planar coupon is disposed at an angle with respect to said fluid flow path in the range between about 0° to about 90°.

23. A corrosion sensor in accordance with claim 14, wherein said housing is an alloy resistant to chemical attack at the temperatures encountered within said fluid flow path.

24. A corrosion sensor in accordance with claim 14, further comprising a ceramic insulator interposed between said housing and said sensing element.

25. A corrosion sensor in accordance with claim 14, further comprising a fitting to secure said sensor to a body containing said fluid flow path.

26. A corrosion sensor in accordance with claim 14, wherein said sensing element is insertable into at least one of a turbine assembly exhaust, a turbine assembly hot gas path, a distillation structure and a refinery.

27. A corrosion sensor in accordance with claim 14, wherein said heating module is configured to contact a first surface of said sensing element opposite to a second surface of said sensing element exposed to said fluid flow path.

28. A corrosion sensor for use within a fluid flow path, said corrosion sensor comprising:
   a wire sensing element;
   a heating module configured to heat said wire sensing element to a predetermined temperature; and
   circuitry coupled to said wire sensing element for generating an electrical current through said wire sensing element and for detecting interruption of electrical continuity through said wire sensing element upon corrosive failure of said wire sensing element.

29. A corrosion sensor in accordance with claim 28, wherein said wire sensing element has a thickness in the range between about 1 mil to about 3 mil.

30. A corrosion sensor in accordance with claim 28, wherein said sensing element comprises a material selected from the group consisting of an alloy, a superalloy, a nickel-based superalloy, a Udimet 700 alloy, and a Rene N5 alloy.

31. A turbine assembly having a fluid flow path, said turbine assembly comprising:
   a compressor;
   a combustor;
   an exhaust section;
   a corrosion sensor for use within said fluid flow path comprising:
      a sensing element;
      a heating module configured to heat said sensing element to a predetermined temperature; and
      circuitry coupled to said sensing element for detecting corrosion of said sensing element.

32. A turbine assembly in accordance with claim 31, wherein said sensing element is selected from the group consisting of an alloy, a superalloy, a nickel-based superalloy, a Udimet 700 alloy, and a Rene N5 alloy.

33. A turbine assembly in accordance with claim 31, wherein said circuitry comprises a processor for generating and detecting a signal through said sensing element.

34. A turbine assembly in accordance with claim 31, wherein said corrosion sensor further comprises a hermetic housing, said sensing element being attached to an external portion of said hermetic housing for exposure to said fluid flow path.

35. A turbine assembly in accordance with claim 31, wherein said heating module is configured to contact a first surface of said sensing element opposite to a second surface of said sensing element exposed to said fluid flow path.

36. A method of detecting corrosion in a fluid flow path, said method comprising the steps of:
   heating a sensor element of a known thickness to a predetermined temperature;
   imposing an oscillating electric filed on said sensor element at said predetermined temperature;
   measuring at least one of an impedance or resistivity of said sensor element;
   exposing said sensor element to a potentially corrosive fluid flow; and
   measuring the change in the at least one of said impedance or said resistivity of said sensor element.

* * * * *